US00PP22462P2

(12) United States Plant Patent
Yates

(10) Patent No.: US PP22,462 P2
(45) Date of Patent: Jan. 17, 2012

(54) ***BEGONIA* PLANT NAMED 'YAMINA'**

(50) Latin Name: *Begonia boliviensis*
Varietal Denomination: Yamina

(76) Inventor: Frederic C. Yates, Congleton (GB)

( * ) Notice: Subject to any disclaimer, the term of this patent is extended or adjusted under 35 U.S.C. 154(b) by 0 days.

(21) Appl. No.: 12/925,550

(22) Filed: Oct. 25, 2010

(51) Int. Cl.
*A01H 5/00* (2006.01)

(52) U.S. Cl. ..... Plt./343
(58) Field of Classification Search ..... Plt./343
See application file for complete search history.

*Primary Examiner* — Annette Para
(74) *Attorney, Agent, or Firm* — Penny J. Aguirre

(57) ABSTRACT

A new cultivar of *Begonia boliviensis* named 'YAMINA', characterized by its large single bright red flowers, its compact, freely branched and pendulant plant habit, and its good tolerance to wind and rain when grown as a bedding plant in open ground. 'YAMINA' has been observed to be mildew free under the conditions grown to date.

2 Drawing Sheets

Botanical classification: *Begonia boliviensis.*
Cultivar designation: 'YAMINA'.

BACKGROUND OF THE INVENTION

The present invention relates to a new and distinct cultivar of *Begonia* plant, botanically known as *Begonia boliviensis* 'YAMINA' and will be referred to hereafter by its cultivar name, 'YAMINA'.

The new cultivar was derived from a controlled breeding program conducted by the inventor at his nursery in Congleton, Cheshire, United Kingdom. The overall purpose of the breeding program is to make selections of *Begonia* plants with compact plant habits suitable for container use combined with superior flower performance and productive stock plants for propagation. 'YAMINA' was selected in the Inventor's greenhouse in 2006 as a single unique plant from amongst the seedlings derived from a cross made between a proprietary plant used in the Inventor's breeding program (not patented) as the female parent and 'YABOS' (U.S. Plant Pat. No. 20,093) as the male parent.

Asexual reproduction of the new cultivar was first accomplished by terminal stem cuttings in Congleton, Cheshire, United Kingdom in 2007 by the Inventor. It has been determined that the characteristics of this cultivar are stable and are reproduced true to type in successive generations.

SUMMARY OF THE INVENTION

The following traits have been repeatedly observed and represent the characteristics of the new cultivar, which in combination distinguish 'YAMINA' as a new and distinct cultivar of *Begonia.*

1. 'YAMINA' exhibits a compact, pendulous plant habit.
2. 'YAMINA' readily produces side shoots.
3. 'YAMINA' exhibits large, single bright red flowers.
4. 'YAMINA' has been observed to be mildew free under the conditions grown to date.
5. 'YAMINA' has shown to be well suited for use as a bedding plant as it is able to withstand rain and wind when planted in open ground.

In comparison to its parents plants; 'YAMINA' differs in having a more compact plant habit, and by exhibiting a greater resistance to powdery mildew to either parent. In addition, 'YABOS' has smaller leaves, smaller flowers and flowers that are paler red in color. 'YAMINA' can be most closely compared to the cultivar 'YASPED' (U.S. Plant patent application Ser. No. 12/657641). 'YASPED' differs from 'YAMINA' in having flowers that are slightly larger and paler in color with tepals that are longer and narrower. 'YAMINA' can also be compared to cultivars from the same breeding program. 'Yagance' (U.S. Plant Pat. No. 19,817) differs most significantly from 'YAMINA' in having bicolor pink and white flowers and 'Yamance' (U.S. Plant Pat. No. 19,777) differs most significantly from 'YAMINA' in having flowers that are pink in color.

BRIEF DESCRIPTION OF THE DRAWING

The accompanying colored photographs illustrate the overall appearance and distinct characteristics of the new *Begonia.* The photographs were taken of plants approximately 6 months in age as grown in 4.5-inch containers under greenhouse conditions under ambient light in the United Kingdom.

The photograph in FIG. 1 was taken in Congelton, United Kingdom and provides a side view of 'YAMINA' in bloom (a basket with two 4.5-inch containers).

Figure 1:
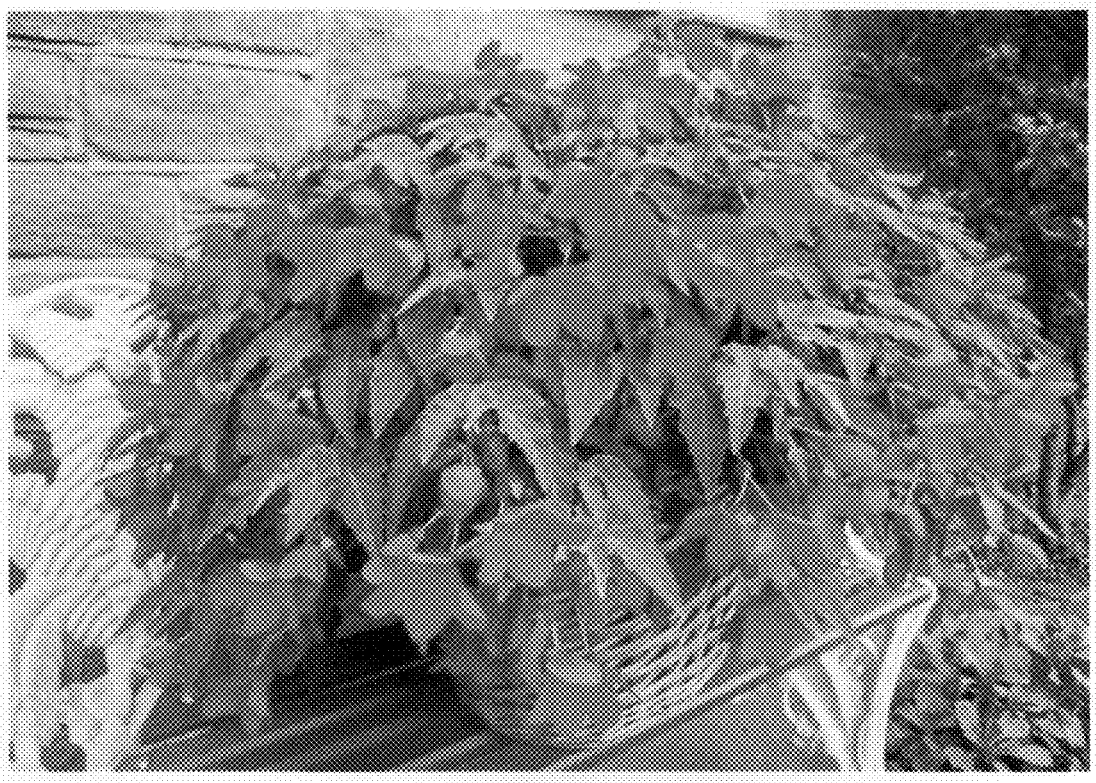
Figure 2:
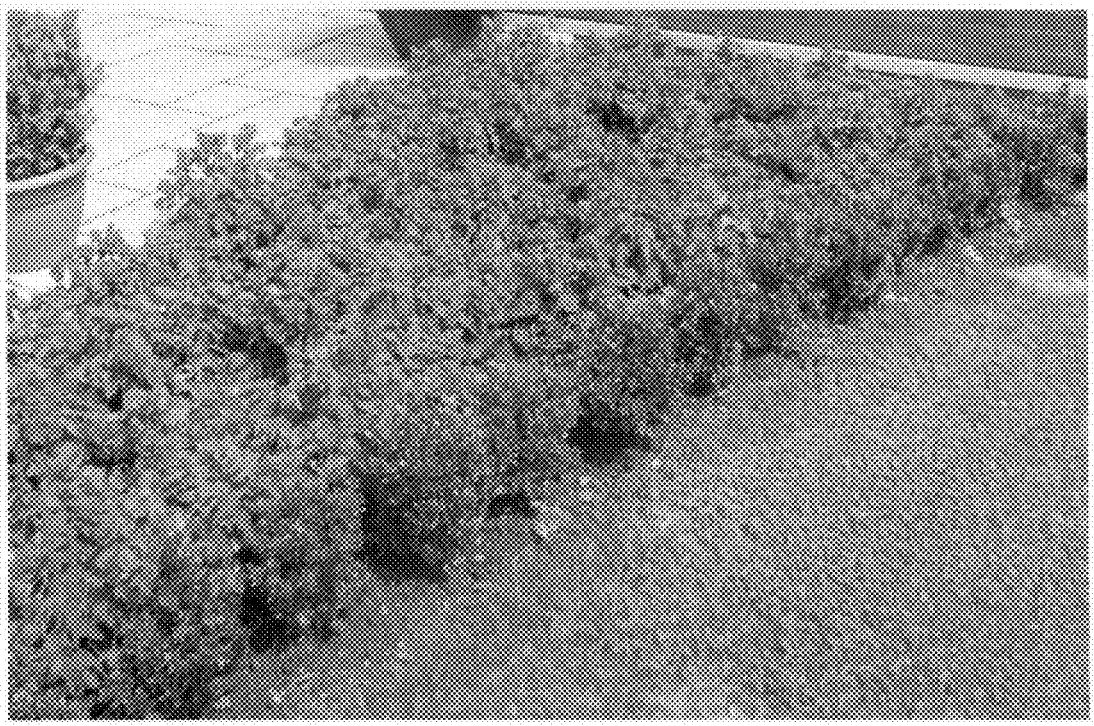

The photograph in FIG. 2 was taken in Warwickshire, United Kingdom and depicts a bed of 'YAMINA' after a severe thunderstorm with high winds.

Figure 3:
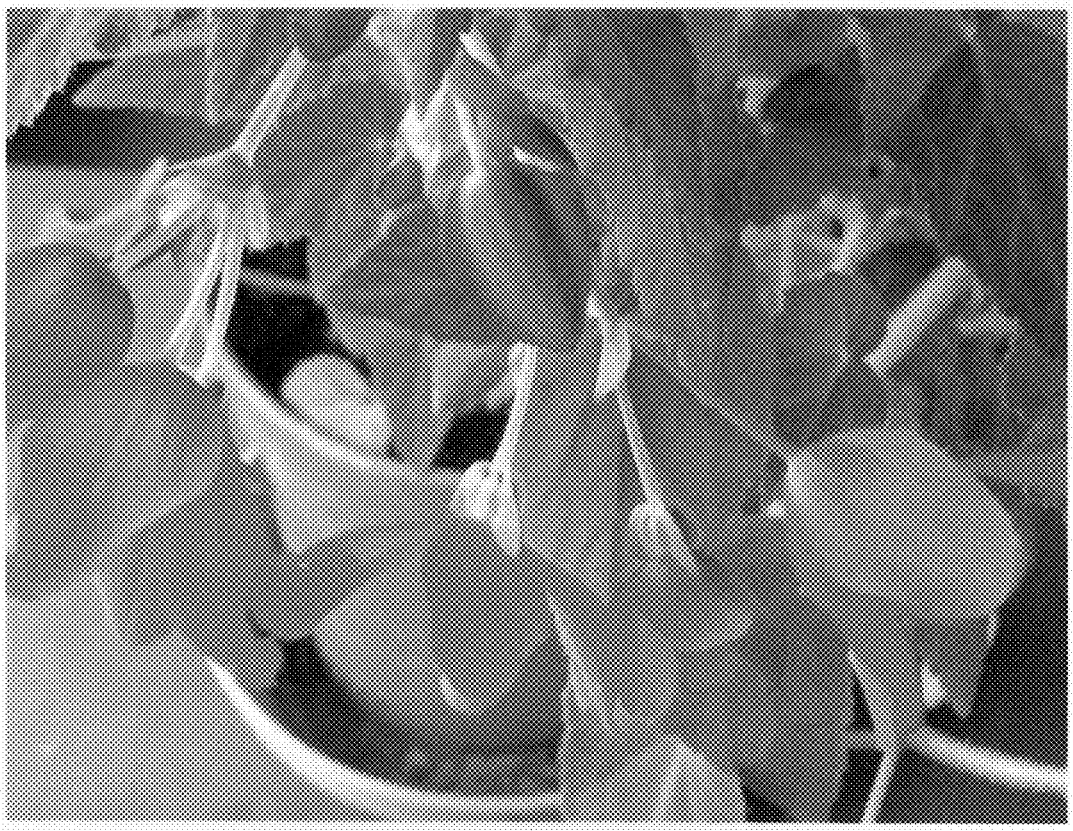
Figure 4:
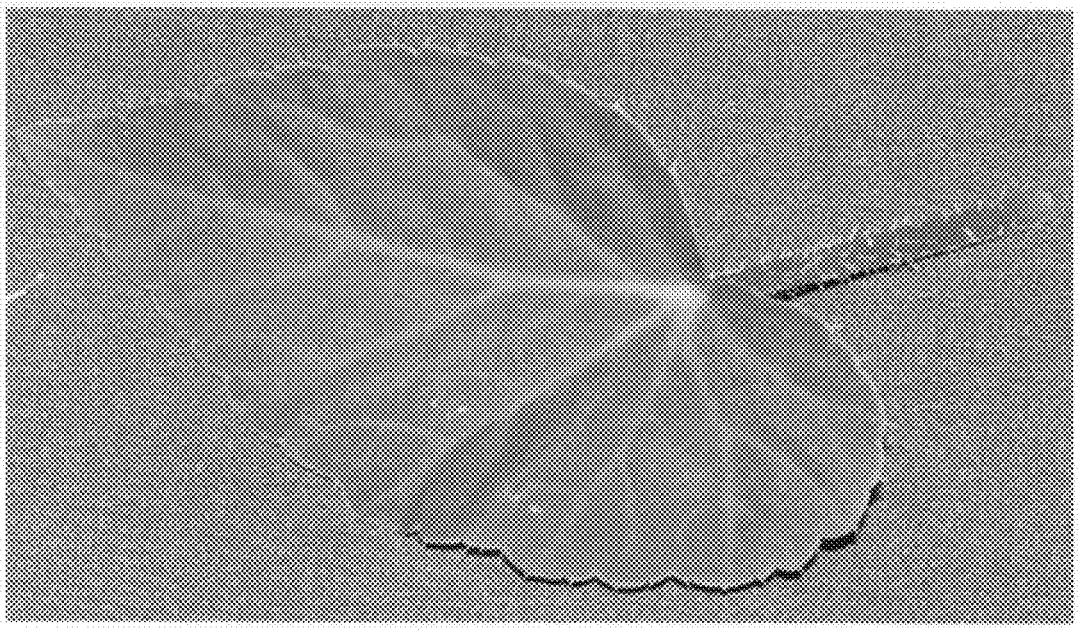

The photographs in FIG. 3 and FIG. 4 were taken in Liss, United Kingdom.

The photograph in FIG. 2 provides a close-up view of the flowers of 'YAMINA'. The photograph in FIG. 3 provides a close-up view of a leaf of 'YAMINA'. The colors in the photograph may differ slightly from the color values cited in the detailed botanical description, which accurately describe the colors of the new *Begonia.*

DETAILED BOTANICAL DESCRIPTION OF THE PLANT

The following is a detailed description of plants of the new cultivar approximately 6 months in age as grown in 4.5-inch containers under greenhouse conditions with ambient light in Congleton, Cheshire, U.K. The phenotype of the new cultivar may vary with variations in environmental, climatic, and cultural conditions, as it has not been tested under all possible environmental conditions. The color determination is in accordance with The 2001 R.H.S. Colour Chart of the Royal Horticultural Society, London, England, except where general color terms of ordinary dictionary significance are used.

General plant characteristics:

*Plant type.*—Deciduous tuberous perennial, grown primarily for use in baskets and containers.

*Plant habit.*—Compact, prostrate and pendulous.

*Flowering period.*—From late March to November.

*Height and spread.*—Reaches about 35 cm in height and about 60 cm in spread.

*Cold hardiness.*—U.S.D.A. Zone 10.

*Culture.*—Grows in any commercial soil or growing media, 12 hours of light is needed for production in the winter months.

*Environmental stresses.*—Shown good tolerance to wind and rain when grown as a bedding plant in open ground.

*Diseases and pests.*—Has been observed to be mildew free under the conditions grown to date.

*Root description.*—Fleshy to fibrous with tubers produced for over-wintering.

*Tubers.*—Irregularly lobed in shape and often depressed in center, an average of 3.5 cm in diameter (larger on older plants), surface is smooth and slightly corky, color between 166D and N167D.

Growth and propagation:

*Growth rate.*—Typical vigor for the species but with more compact growth.

*Propagation.*—Terminal stem cuttings.

*Time required for root initiation.*—10 to 14 days at 20° C.

*Time required for root development.*—5 to 8 weeks to reach commercial size.

Stem description:

*Stem size.*—Average of 28 cm in length and 9 mm in width with lateral branches about 4 mm in width.

*Stem shape.*—Round, solid.

*Stem color.*—179C, becoming 179B.

*Stem surface.*—Glabrous but weakly glaucous, with coarse bristly pubescence, lenticels absent.

*Internode length.*—Average of 4.5 cm.

*Branching habit.*—Freely branched.

*Branching angle at emergence.*—About 45°.

Foliage description:

*Leaf shape.*—Strongly asymmetric, one side narrow ovate, the other narrow cordate and wider.

*Leaf division.*—Entire.

*Leaf base.*—Rounded on narrower side, cordate on wider side.

*Leaf apex.*—Acuminate.

*Leaf venation.*—Pinnate, color 137C on upper surface and 147B on lower surface.

*Leaf margins.*—Irregularly notched with occasional bristly hairs.

*Leaf attachment.*—Petiolate.

*Leaf arrangement.*—Alternate.

*Leaf surface.*—Upper surface; glabrous, smooth, lower surface; glabrous on blade and very weakly pubescent on mid vein.

*Leaf color.*—Upper surface; 137D, lower surface; 147C tinged with 181B.

*Leaf size.*—Average of 8.5 cm in length and 3.5 cm in width.

*Leaf quantity.*—Average of 14 per branch.

*Leaf fragrance.*—None.

*Petioles.*—About 2.3 cm in length and 2 mm in width, surface is pubescent with simple hairs, color is 170D.

*Stipules.*—Triangular in shape, 168B in color and rapidly becoming dry and papery, about 5 mm in length and 3 mm in width.

Flower description:

*Inflorescence type.*—2 to 3 flowered cyme produced sequentially in the axils of the upper leaves, monoecious with terminal male flowers developing before the lateral female flowers.

*Peduncles.*—About 4.3 cm in length and 2 mm in width, color; 41A on upper surface, 34D on lower surface becoming 160C towards base, surface is pubescent with long simple hairs.

*Flower persistence.*—Self-cleaning.

*Flower type.*—Single.

*Flower fragrance.*—None.

*Flower number.*—Average of 10 flowers per stem are open at one time on mature plants.

*Flower aspect.*—Hanging.

*Bracts.*—2, present at base of cyme, broad ovate in shape, acute bifid apex, about 1.1 cm in length and 1.2 cm width, color is 195A becoming 47B at margins.

Male flowers:

*Pedicels.*—About 2.6 cm in length and 1 mm in width, color; 41A on upper surface, 34D on lower surface, slightly pubescent surface.

*Flower buds.*—Flattened ovoid in shape, about 2.4 cm in length and 1.9 cm in width, 46B in color.

*Flower size.*—About 3.8 cm in length and 5.5 cm in width.

*Tepals.*—4 in number (2 inner and 2 outer), outer tepals; broad ovate in shape, recurved near the apex, obtuse apex, rounded base, average of 3.5 cm in length and 2.1 cm in width, glabrous and smooth surface, entire margin, color; inner and outer surface 46B becoming 41A at base.

*Corolla form.*—Spreading, tepals are un-fused.

*Stamens.*—Numerous, connate below forming a tube, about 1.6 cm in length and 1.5 mm in width, 14B in color.

*Filaments.*—About 3 mm in length and 0.5 mm in width, 14B in color.

*Anthers.*—Broadly elliptic in shape, about 1 mm in length and 1 mm in width, 14B in color.

*Pollen.*—Abundant in quantity, 8C in color.

Female flowers:

*Pedicels.*—About 2.8 cm in length and 1 mm in width, color; 41A on upper surface, 34D on lower surface, slightly pubescent surface.

*Flower buds.*—Flattened ovoid in shape, about 1.9 cm in length and 1.4 cm in width, 46B in color.

*Flower size.*—About 3.1 cm in length and 5.2 cm in width.

*Tepals.*—5 in number (3 inner and 2 outer), outer tepals; ovate in shape, obtuse apex, rounded base, average of 2.9 cm in length and 1.8 cm in width, glabrous and smooth surface, entire margin, color; inner and outer surface 45C becoming 45D at base, inner tepals; narrow obovate in shape, recurved near the apex, obtuse apex, narrowly cuneate base, average of 3 cm in length and 1.4 cm in width, glabrous and smooth surface, entire margin, color; inner and outer surface 45C becoming 45D at base.

*Corolla form.*—Spreading, tepals are un-fused.

*Styles.*—3 in number, cylindrical, connate for basal 1 mm, about 4 mm in length and 1 mm in width, 45B in color.

*Stigmas.*—Bifid in shape, lobes about 4 mm in length and 1 mm in width, N23B in color.

*Ovaries.*—Inferior, about 8 mm in length and 7 mm in width (excluding wings), color is 144D flushed 179B merging to 47B at tips of the wings.

*Seed.*—Very numerous, ovoid in shape, 165C in color, extremely small in size.

It is claimed:

1. A new and distinct cultivar of *Begonia* plant named 'YAMINA' as herein illustrated and described.

* * * * *